United States Patent
Owechko et al.

(10) Patent No.: US 10,234,377 B1
(45) Date of Patent: Mar. 19, 2019

(54) FUSION OF INDEPENDENT COMPONENT ANALYSIS AND SPARSE REPRESENTATION-BASED CLASSIFICATION FOR ANALYSIS OF SPECTRAL DATA

(71) Applicant: HRL Laboratories, LLC, Malibu, CA (US)

(72) Inventors: Yuri Owechko, Newbury Park, CA (US); Shankar R. Rao, Agoura Hills, CA (US)

(73) Assignee: HRL Laboratories, LLC, Malibu, CA (US)

( * ) Notice: Subject to any disclaimer, the term of this patent is extended or adjusted under 35 U.S.C. 154(b) by 129 days.

(21) Appl. No.: 15/280,575

(22) Filed: Sep. 29, 2016

Related U.S. Application Data

(60) Provisional application No. 62/234,653, filed on Sep. 29, 2015.

(51) Int. Cl.
  *G01J 3/42* (2006.01)
  *G01N 21/27* (2006.01)
  *G01N 21/35* (2014.01)

(52) U.S. Cl.
  CPC .......... *G01N 21/27* (2013.01); *G01N 21/35* (2013.01); *G01N 2201/06113* (2013.01)

(58) Field of Classification Search
  CPC ....... G01J 3/42; G01N 21/35; G01N 21/3581; G01N 2021/1793
  See application file for complete search history.

(56) References Cited

U.S. PATENT DOCUMENTS

| | | | | |
|---|---|---|---|---|
| 6,853,452 B1 * | 2/2005 | Laufer | .............. | G01N 21/3504 356/436 |
| 2003/0161527 A1 * | 8/2003 | Wang | .................. | G06K 9/0014 382/156 |
| 2004/0252300 A1 * | 12/2004 | Slater | ....................... | G01J 3/42 356/318 |
| 2009/0022336 A1 * | 1/2009 | Visser | ................. | G10L 21/0272 381/94.7 |
| 2011/0213566 A1 * | 9/2011 | Kopriva | ................. | G06K 9/624 702/28 |
| 2013/0297296 A1 * | 11/2013 | Yoo | ..................... | G10L 21/0272 704/203 |

OTHER PUBLICATIONS

Bruckstein et al. describe sparsity-optimizing L1 norm minimization in "From Sparse Solutions of Systems of Equations to Sparse Modeling of Signals and Images," SIAM Review, vol. 51, No. 1, pp. 34-81, 2009.

(Continued)

*Primary Examiner* — Mischita L Henson
(74) *Attorney, Agent, or Firm* — Tope-McKay & Associates

(57) ABSTRACT

Described is a system for remote analysis of spectral data. A set of measured spectral mixtures are separated using a blind demixing process, resulting in demixed outputs. A demixed output is selected for further processing, and a spectral library is selected from a set of spectral libraries that is specialized for the selected demixed output. Individual components in the selected demixed output are classified via a non-blind demixing process using the selected spectral library. Trace chemical residues are detected in the set of measured spectral mixtures.

18 Claims, 8 Drawing Sheets

(56) References Cited

OTHER PUBLICATIONS

J. Cardoso in "High-order contrasts for independent component analysis," Neural Computation, vol. 11, No. 1, pp. 157-192, 1999.
Wright, A. Yang, A. Ganesh, S. Sastry, and Y. Ma in "Robust Face Recognition via Sparse Representation," IEEE Trans. on Pattern Analysis and Machine Intelligence (TPAMI), vol. 31. No. 2, pp. 210-227, 2009.
S. Lloyd in "Least squares quantization using PCM," IEEE Trans. on Info. Theory, vol. 28, No. 2, pp. 129-137, 1982.
Wagner et al. in "Towards a Practical Face Recognition System: Robust Alignment and Illumination by Sparse Representation," IEEE Trans. on Pattern Analysis and Machine Intelligence (TPAMI), vol. 34, No. 2, pp. 372-386, 2012.
URI Explosives Database. http://expdb.chm.uri.edu/ Site last updated on May 1, 2014.

* cited by examiner

FUSION OF INDEPENDENT COMPONENT ANALYSIS AND SPARSE REPRESENTATION-BASED CLASSIFICATION FOR ANALYSIS OF SPECTRAL DATA

CROSS-REFERENCE TO RELATED APPLICATIONS

This is a Non-Provisional patent application of 62/234,653, filed in the United States on Sep. 29, 2015, entitled, "Fusion of Independent Component Analysis and Sparse Representation and Classification for Analysis of Spectral Data," the entirety of which is hereby incorporated by reference.

BACKGROUND OF INVENTION

(1) Field of Invention

The present invention relates to a system for spectral demixing and, more particularly, to a system for spectral demixing using a combination of Independent Component Analysis (ICA) and Sparse Representation-based Classification (SRC) to analyze the signals.

(2) Description of Related Art

The detection and analysis of trace chemical residues on surfaces, such as car doors or packages from long stand-off distances (e.g., greater than 1 meter) have not been achievable to date using existing laser-based optical spectroscopy methods due to the high clutter rejection and sensitivity required. Independent Component Analysis (ICA) is a known algorithm for separating a set of mixtures of signals into the constituent components by optimizing a measure of the statistical independence of the outputs. It relies on the components being statistically independent, but does not use prior knowledge of the signals (i.e., it operates blindly). Further, spectral demixing is a field in which a variety of signals are separated. An advantage to separating signals is that target spectral signals can be separated from each other and from clutter and noise.

The detection and analysis of trace chemical residues on surfaces from long stand-off distances has not been achievable to date using existing laser-based optical spectroscopy methods due to the high clutter rejection and sensitivity required. Existing algorithmic solutions for stand-off chemical spectrum demixing and identification have utilized methods borrowed from hyperspectral analysis, such as vertex component analysis, pixel purity index, and N-FINDR, or standard spectrographic methods such as principal component analysis (PCA), cross-correlation, partial least squares (PLS), and multivariate curve resolution alternate least squares (MCR-ALS). These methods involve both a human in the loop and various assumptions, such as the availability of pure material regions to serve as references, which make them inappropriate for automated remote detection of materials and chemical residues.

Thus, a continuing need exists for a system that can separate mixtures from long distances without previous knowledge of the mixture components.

SUMMARY OF INVENTION

The present invention relates to a system for spectral demixing and, more particularly, to a system for spectral demixing using a combination of Independent Component Analysis (ICA) and Sparse Representation-based Classification (SRC) to analyze the signals. The system comprises one or more processors and a memory having instructions such that when the instructions are executed, the one or more processors perform multiple operations. A set of measured spectral mixtures are separated using a blind demixing process, resulting in a plurality of demixed outputs. A demixed output is selected for further processing. A spectral library in a set of spectral libraries is selected that is specialized for the selected demixed output. Individual spectral components in the selected demixed output are classified via a non-blind demixing process using the selected spectral library. Trace chemical residues are detected in the set of measured spectral mixtures.

In another aspect, the blind demixing process is an Independent Component Analysis (ICA) process, and the non-blind demixing process is a Sparse Representation-based Classification (SRC) process.

In another aspect, combined use of the ICA process and the SRC process separates spectra from the set of measured spectral mixtures and noise prior to classification of individual spectral components.

In another aspect, the at least one demixed output, having a plurality of spectral features, is selected for further processing by the SRC process using similarity of spectral features of the at least one demixed output to a target spectra.

In another aspect, spectral features in the selected demixed output are used to select the spectral library specialized for the selected demixed output.

In another aspect, a separate SRC process is used on each selected demixed output, and the SRC processes are processed in parallel on multiple processors.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
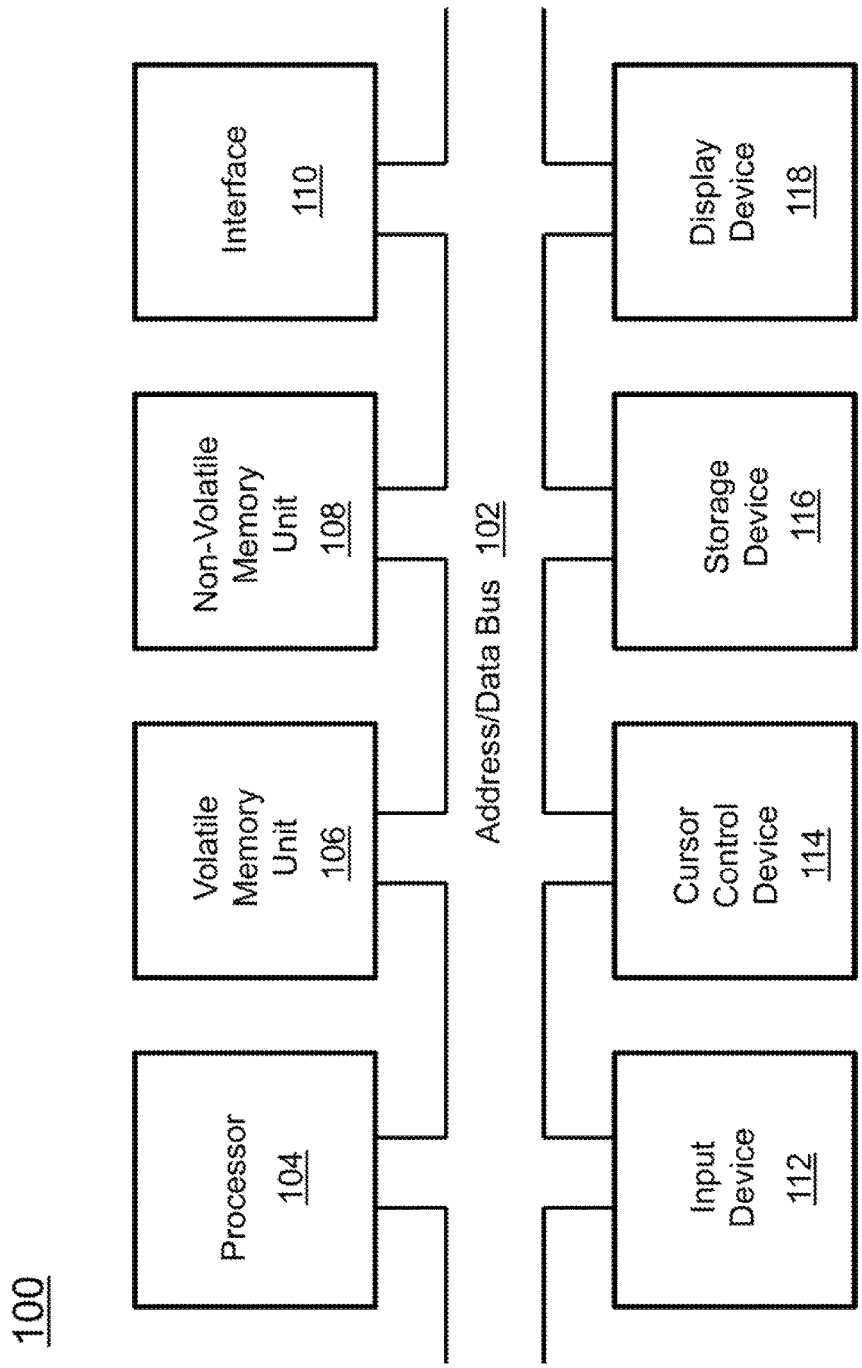
FIG. 1 is a block diagram depicting the components of a system for spectral demixing according to some embodiments of the present disclosure.

The present invention relates to a system for spectral demixing and, more particularly, to a system for spectral demixing using a combination of Independent Component Analysis (ICA) and Sparse Representation-based Classification (SRC) to analyze the signals.

The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, a description of the various principal aspects of the present invention is provided. Subsequently, an introduction provides the reader with a general understanding of the present invention. Finally, specific details of the present invention are provided to give an understanding of the specific aspects.

(1) Principal Aspects

Various embodiments of the invention include three "principal" aspects. The first is a system for spectral demixing. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
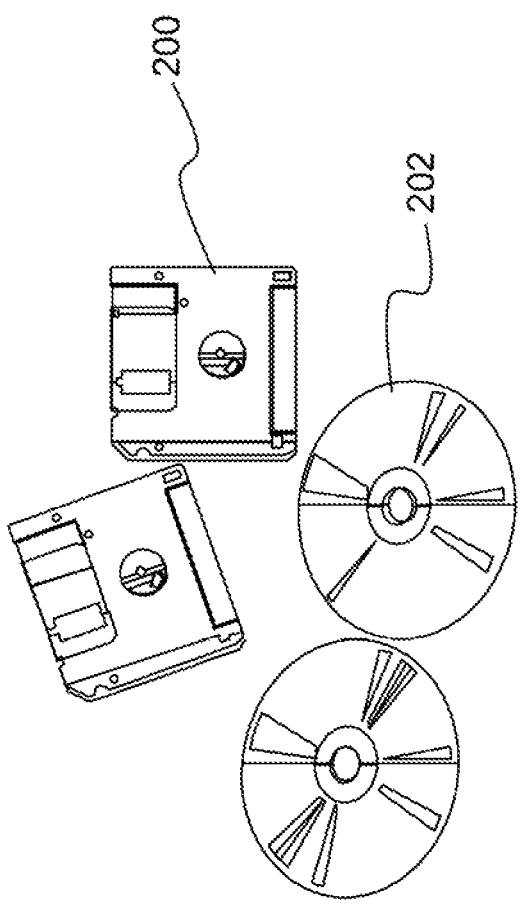
FIG. 2 is an illustration of a computer program product according to some embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(2) Introduction

Sparse Representation-based Classification (SRC) models a multi-dimensional signal as a sparse mixture of known library elements by maximizing the sparsity of representation while maintaining the fidelity of the mixture model. These library elements depend on the nature of the signals. For infrared (IR) spectroscopy, they are examples of the chemical spectra of individual substances. SRC also models possible deformations of the signal that can occur during the measurement process. Since ICA and SRC utilize almost orthogonal types of information, using ICA as a front-end for SRC results in a very low net false alarm rate that is close to the product of the individual false alarm rates for ICA and SRC. The ICA-SRC combination also separates spectra from different materials, such as, for example, explosives and commonly occurring surface materials such as plastics, and noise before final classification is performed, which greatly increases clutter rejection and increases sensitivity (e.g., the minimum detectable concentration of a substance), because of the increased signal to noise ratio.

ICA and SRC were developed for different applications. ICA is used primarily for analysis of one-dimensional (1-D) signals, such as audio mixtures or spectra, and also for some image processing applications. SRC, however, was developed by workers in computer vision for recognizing structured two-dimensional (2D) images, such as faces, in a robust way that can compensate for variabilities due to changes in illumination or pose. The system described herein bridges these two fields and uses ICA to separate mixtures of spectra (i.e., a continuous sequence or range) before classification by SRC in a robust way that can compensate for spectral variability due to different measurement conditions. These mixtures can consist, for example, of mixtures of targeted materials, such as explosive residues with commonly occurring background materials.

(3) Specific Details of Various Embodiments of the Invention

An important and challenging initial step in the remote detection of chemical residues using optical spectroscopy is separation or demixing of the spectral features of target compounds from mixtures containing noise and features of the clutter. The target features, such as the locations, amplitudes, and widths of peaks in the spectra, may be small relative to the clutter, and they may be mixed with features of other targets or unknown materials. The spectra of targets can also be deformed depending on the substrate, the particular residue, and the probe laser angle of incidence. Described below is an algorithmic framework for extraction and classification of target spectra from such mixtures.

The system according to embodiments of the present disclosure performs spectral demixing-separating the target spectral signals from each other and from clutter and noise—based on a unique combination of Independent Component Analysis (ICA) and Sparse Representation-based Classification (SRC) to analyze the signals. Clutter is defined as a spectral signature from background materials that are not of interest for detection but can obscure the target signal. Noise is a random signal without structure that arises from the limited dynamic range of detectors. The detection and analysis of trace chemical residues on surfaces from long stand-off distances has not been achievable to date using existing laser-based optical spectroscopy methods due to the high clutter rejection and sensitivity required. The system described herein uses ICA to exploit the statistical independence of spectra over wavelengths to separate mixtures "blindly" or without knowledge of the mixture components. Blind demixing separates both known targets and unknown clutter, and also denoises the separated components. In some embodiments, the invention uses SRC to model the outputs of ICA as a combination of elements from a spectral library for final classification of the mixture components using sparsity-optimizing $L_1$ norm minimization. Bruckstein et al. describe sparsity-optimizing $L_1$ norm minimization in "From Sparse Solutions of Systems of Equations to Sparse Modeling of Signals and Images," SIAM Review, Vol. 51, No. 1, pp. 34-81, 2009, which is hereby incorporated by reference as though fully set forth herein.

The approach according to some embodiments of the present disclosure is based on using a blind source separation method, such as independent component analysis (ICA), that does not have any knowledge of targets or clutter as the front end for non-blind sparse representation and classification (SRC). As described above, ICA is an algorithm for separating a set of mixtures of signals into the constituent components by optimizing a measure of the statistical independence of the outputs, as described by J. Cardoso in "High-order contrasts for independent component analysis," Neural Computation, Vol. 11, No. 1, pp. 157-192, 1999 (hereinafter referred to as Cardoso), which is hereby incorporated by reference as though fully set forth herein. It relies on the components being statistically independent, but does not use prior knowledge of the signals (i.e., it operates blindly).

SRC separates and identifies mixture components by modeling the mixture using a spectral library and $L_1$ norm minimization. It can also include compensation of nonlinear spectral deformations due to substrate variations in its modeling. SRC models a signal as a sparse mixture of known library elements by maximizing the sparsity of representation while maintaining the fidelity of the mixture model. Additionally, it can model possible deformations of the signal that can occur during the measurement process. SRC is described in detail by Wright, A. Yang, A. Ganesh, S. Sastry, and Y. Ma in "Robust Face Recognition via Sparse Representation," IEEE Trans. on Pattern Analysis and Machine Intelligence (TPAMI), Vol. 31. No. 2, 2009 (hereinafter referred to as Wright et al.), which is hereby incorporated by reference as though fully set forth herein.

Since ICA and SRC utilize almost orthogonal types of information, using ICA as a front-end filter for SRC results in a very low net false alarm rate that is close to the product of the individual false alarm rates for ICA and SRC. The ICA-SRC combination also separates spectra from different materials and noise before final classification is performed, which greatly increases clutter rejection and increases sensitivity because of the increased signal to noise ratio.

Figure 3:
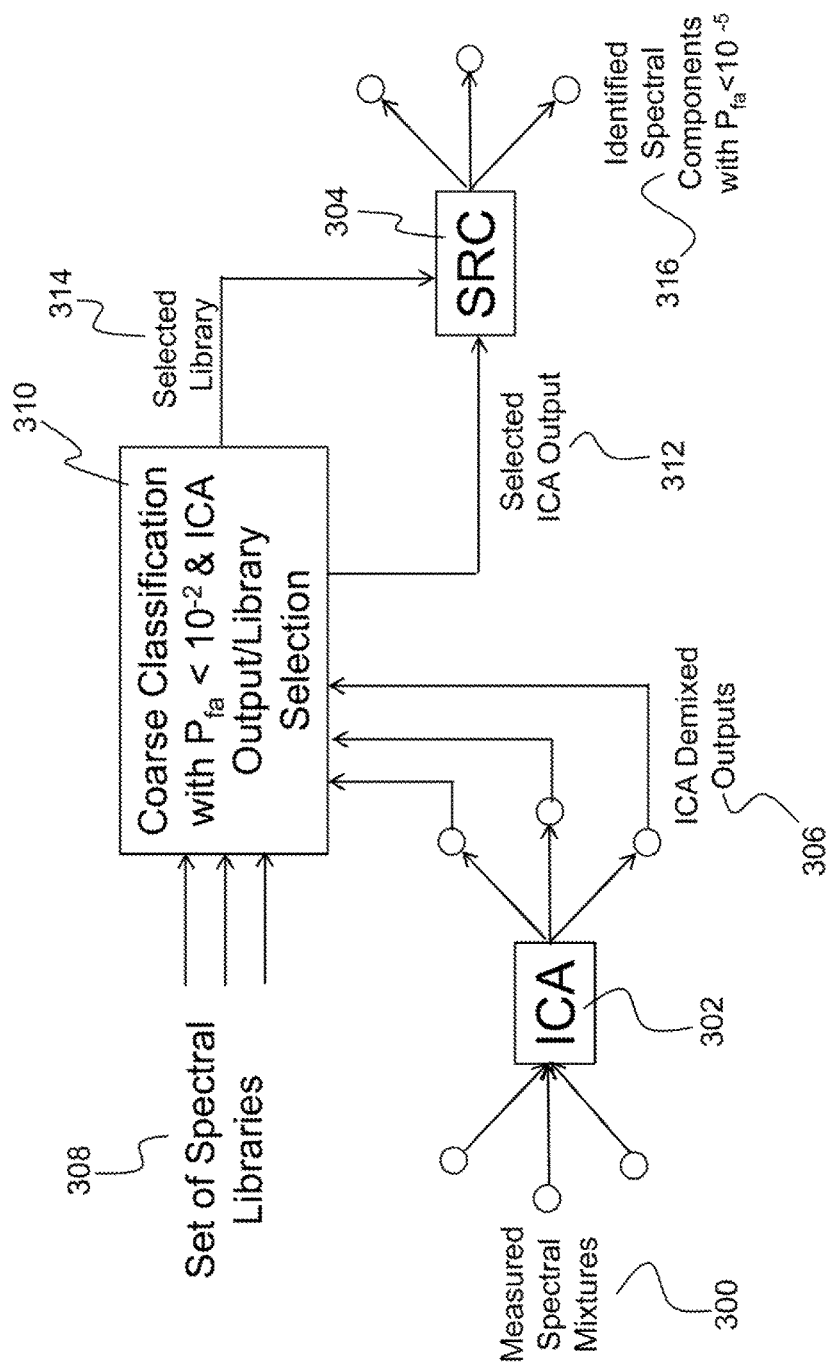
FIG. 3 is a diagram illustrating the fusion of blind demixing using independent component analysis (ICA) with spectral library-based sparse representation and classification (SRC) according to some embodiments of the present disclosure.

FIG. 3 shows the method for combining blind demixing of measured spectral mixtures 300 (which can consist, for example, of mixtures of chemical explosive residue with background materials) using ICA 302 with spectral library-based SRC 304 according to embodiments of the present disclosure. It is assumed that ICA 302 will not perform perfect demixing so the ICA demixed outputs 306 will contain residual mixtures of spectra that are not completely independent due to their residual similarity. The spectral library is clustered or organized by spectral similarity using well-known methods, such as k-means, to create a set of spectral libraries 308 for groups of similar spectra. k-means is described by S. Lloyd in "Least squares quantization using PCM," IEEE Trans. on Info. Theory, Vol. 28, No. 2, pp. 129-137, 1982, which is hereby incorporated by reference as though fully set forth herein. Similarity can be measured using Euclidean or angular distance measures. Similarity can also be measured using the inner product of the output with reference spectra. The initial classification of the ICA outputs 310 into one of the spectral clusters is used to select both the ICA output(s) for further processing (i.e., selected ICA output 312) and the library(s) specialized for the output(s) (i.e., selected library 314) for further separation of the mixture components. The features are used to select the next level of decomposition of the output into components representing sub-categories of spectra. A selected library 314 is then used by SRC 304 to identify the individual spectral components 316.

Figure 6:
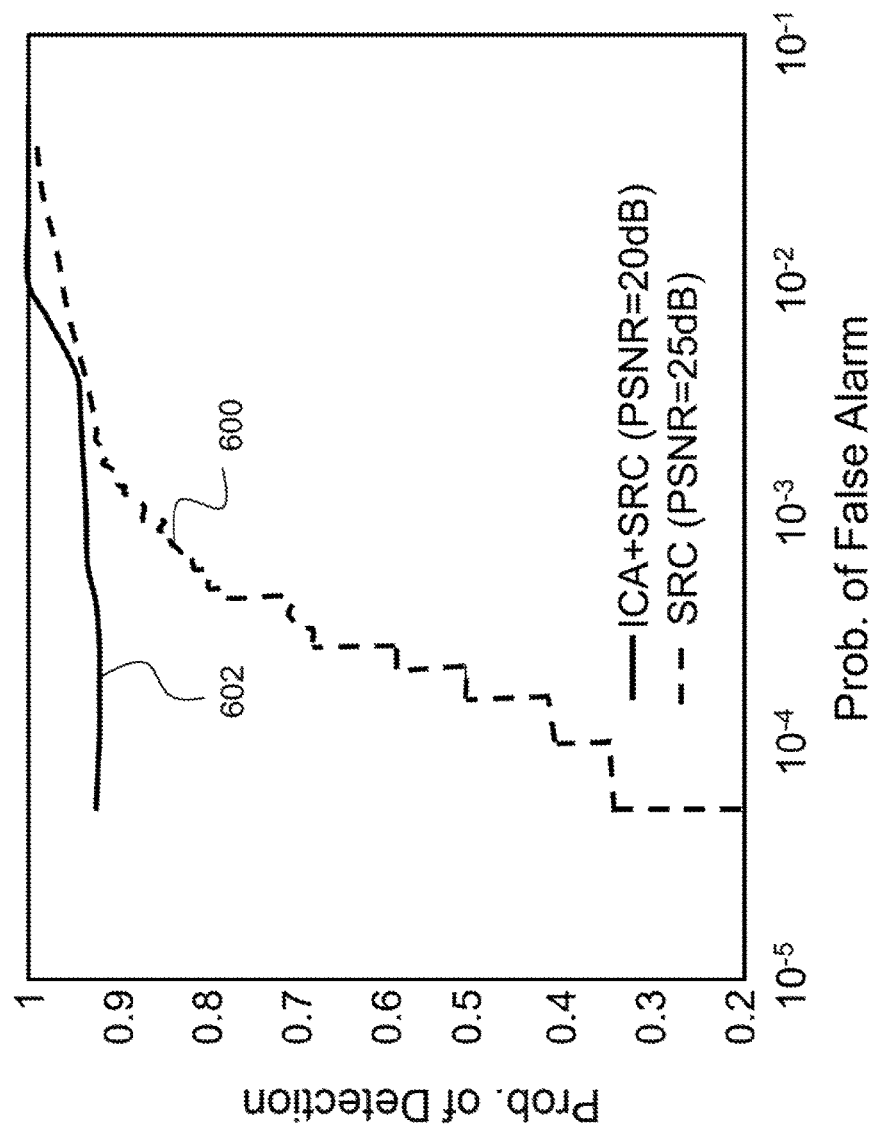
FIG. 6 is an illustration of results from simulations demonstrating a large performance increase possible when ICA is used to pre-filter the input to the SRC detection process according to some embodiments of the present disclosure.

Since ICA demixing is based on the statistical independence of component spectra, while SRC models the mixtures using a library, the two methods are based on completely different types of information. Therefore, one can expect their false alarm mechanisms to be uncorrelated so that the total $P_{fa}$ (probability of false alarm) will be close to the product of the individual $P_{fa}$s. This will greatly reduce the effective $P_{fa}$ for the same measurement PSNR (peak signal to noise ratio). Since ICA and SRC $P_{fa}$s in the $10^{-2}$ range have been demonstrated in experimental simulations for measurement PSNR>20 decibels (dB), the combined $P_{fa}$ is expected to be lower than $10^{-4}$ for PSNR=20 dB. Specifically, the fusion of blind demixing using ICA with spectral library-based SRC reduces $P_{fa}$ to the $10^{-5}$ range. Also demonstrated is the rejection of clutter up to 100× the target strength separately for ICA and SRC, so the different demixing principles of ICA and SRC will also enable the combination to increase the clutter rejection ratio for the same PSNR or maintain it for lower PSNR. This is illustrated in FIG. 6 which shows the improvement in probability of detection obtained when ICA is used as a preprocessing stage for SRC. Each of these aspects is described in further detail below.

(3.1) Adaptive Blind Demixing

The goal of blind demixing algorithms is to separate out large-magnitude background clutter from target mixtures in an unsupervised fashion (i.e., without the use of a library of spectra). This enables the system according to embodiments of the present disclosure to robustly identify components in mixtures contaminated by clutter spectra not present in the library. In addition, blind demixing significantly increases the PSNR of component mixtures by removing both noise and large magnitude clutter from components.

Figure 4A:
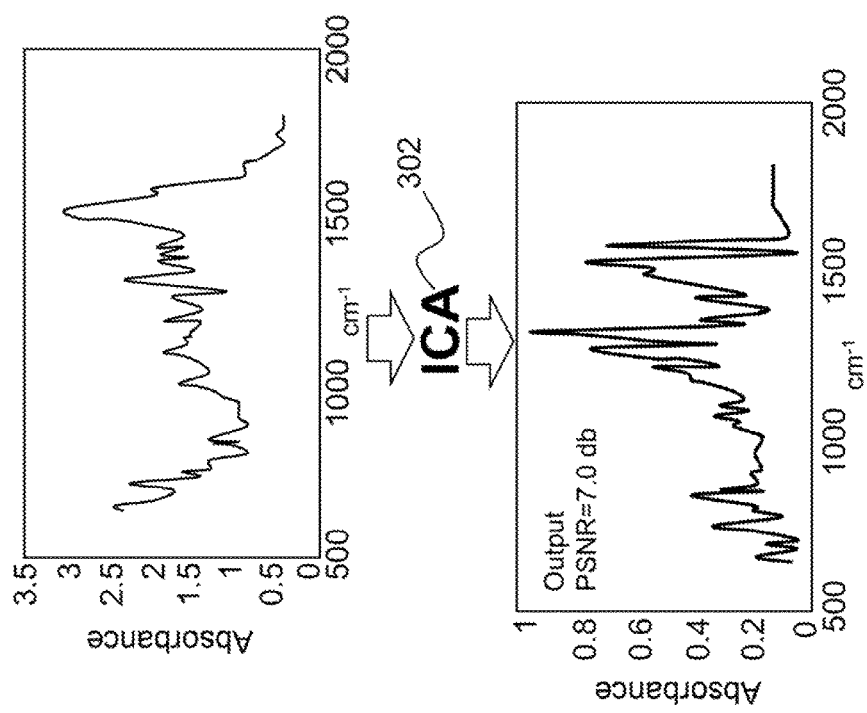
FIG. 4A is an illustration of an example of denoising and clutter rejection for clutter IX stronger than targets using ICA blind demixing according to some embodiments of the present disclosure.
Figure 4B:
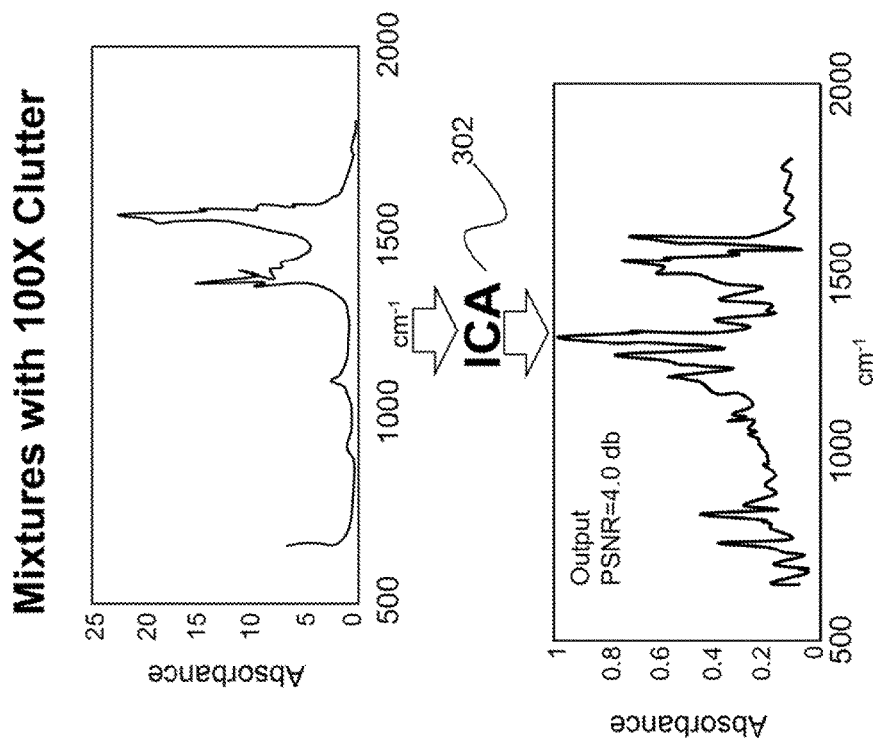
FIG. 4B is an illustration of an example of denoising and clutter rejection for clutter 100× stronger than targets using ICA blind demixing according to some embodiments of the present disclosure.
Figures 4C, 4D:
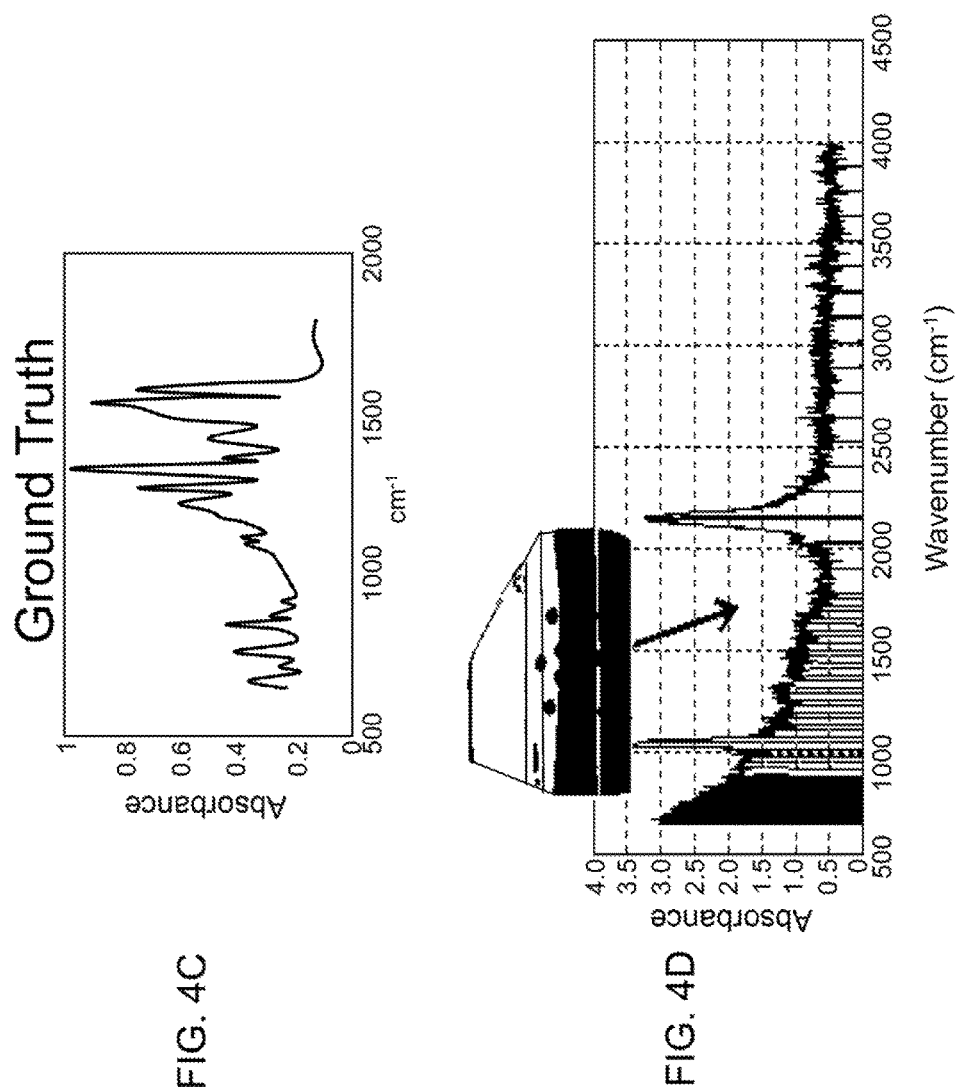
FIG. 4C is an illustration of an example of a ground truth for the samples used in FIGS. 4A and 4B according to some embodiments of the present disclosure.
FIG. 4D is an illustration of foveated spectral sampling of input mixtures according to some embodiments of the present disclosure.

FIGS. 4A-4C depict examples of experimental simulation results for blind denoising and demixing of spectral mixtures using the JADE implementation of ICA (Cardoso). Five spectra from the University of Rhode Island (URI) explosives database were added together to form 20 mixtures with random weightings selected from a uniform distribution of weights between 0 and 1. One of the spectra was arbitrarily designated as clutter and its strength was increased by 1× (FIG. 4A) and 100× (FIG. 4B) relative to the targets. In this case, one of the explosives spectra was selected to be clutter for a worst case test of the algorithm since they have similar characteristics. Noise was also added to the mixtures to simulate a measurement PSNR of 15 dB or 20 dB. In FIGS. 4A and 48, target components (lower plots) were extracted from spectral mixtures formed using the 5 spectra (upper plots) from the University of Rhode Island explosives spectral dataset. In both cases, the outputs (lower plots of FIGS. 4A and 4B) are very close to the ground truth (FIG. 4C). Spectrally variable or "foveated" spectral sampling of the input mixtures is shown in FIG. 4D. The illustrated spectrum is measured at one of the shown spots on the vehicle in this example. The vertical lines indicate where in wavenumber sampling of the spectrum was performed. Finer spaced sampling was used at the lower wavenumbers where the spectral peaks tend to be narrower. This foveation reduced the number of measurements by 6.6× relative to uniform sampling without compromising the reconstruction quality.

Figures 5A, 5B:
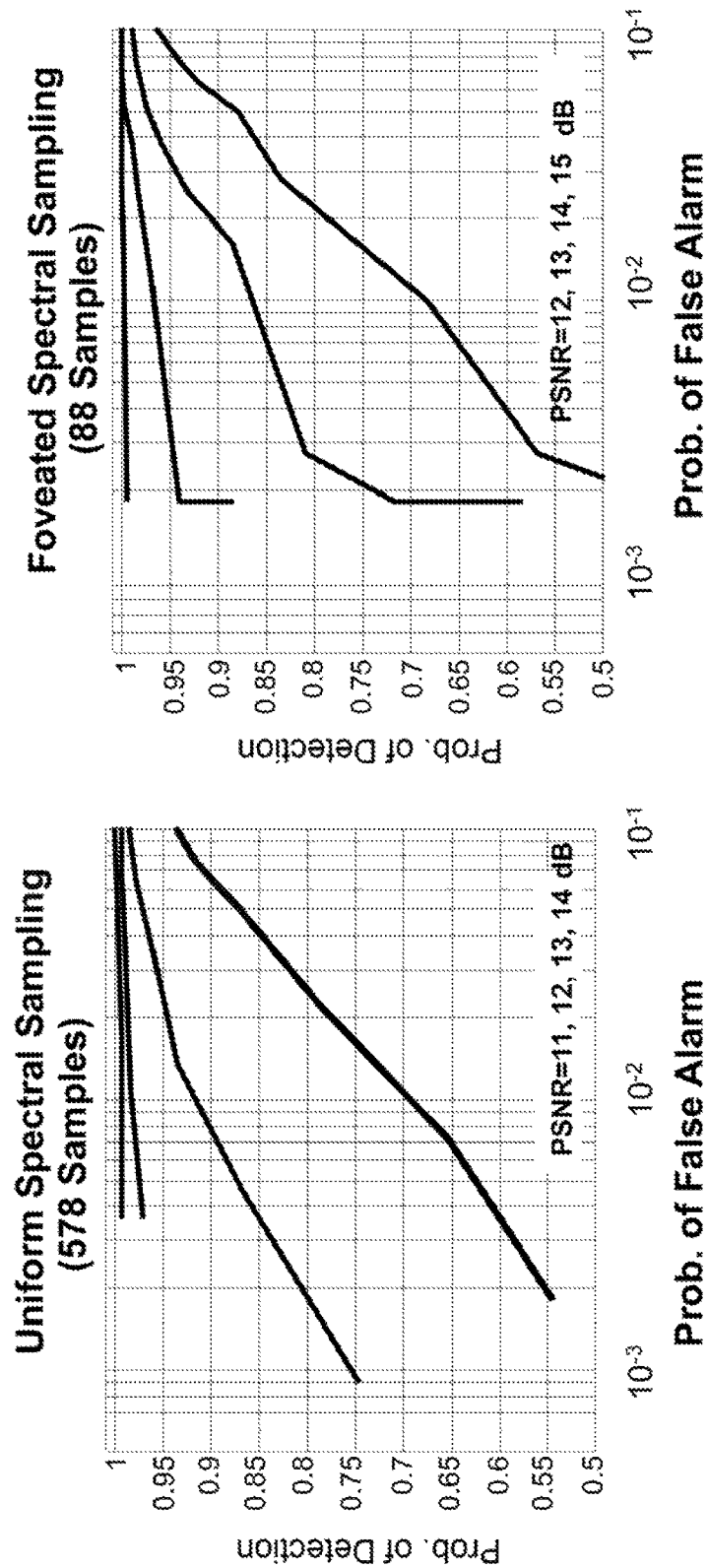
FIG. 5A is an illustration of the effects of uniform spectral sampling according to some embodiments of the present disclosure.
FIG. 5B is an illustration of the effects of spectral foveation on recognition of ICA outputs according to some embodiments of the present disclosure.

FIGS. 5A and 5B depict the effects of spectral foveation on recognition of the ICA outputs in FIGS. 4A and 4B using a nearest neighbor classifier based on the 44 member URI explosives spectral library. The foveation (FIG. 5B) reduced the number of measurements by 6.6× while increasing the required measurement PSNR by only 1 to 2 dB. As shown in FIGS. 5A and 5B, the component spectra were successfully extracted from the mixtures using the JADE ICA algorithm without using any prior knowledge of the components or background, as evidenced by the $P_d$ (probability of detection) vs. $P_{fa}$ (probability of false alarm) performance curves for nearest neighbor classification of the ICA outputs for different measurement PSNR values for both non-uniform sparse sampling (foveation, FIG. 5B) and uniform spectral sampling (FIG. 5A). The curves in FIGS. 5A and 5B represent different PSNR values. The small representation degradation due to foveation could be compensated by increasing the measurement PSNR by only 1 or 2 dB. In experimental simulations, the system described herein was able to reject clutter that was 100× stronger than the targets using ICA and assuming a measurement PSNR of 20 dB.

(3.2) Sparse Representation-Based Classification for Modeling Spectral Mixtures and Deformations Described in this section is a non-blind demixing process based on sparse representation-based classification (SRC) of a single spectral mixture using spectral library components to model the mixture. SRC is robust to noise, performs identification as part of the demixing process, and can model and correct for certain kinds of nonlinear deformations such as the effects of different substrates on measured target spectra. As described above, the ICA blind demixing method can be used as a pre-processing step to provide cleaned up inputs for SRC.

Recently, the machine learning community has examined pattern recognition within a sparse representation-based classification (SRC) framework. The basic approach was first proposed by Wright et al. Wright et al. stipulates that even with an extremely low sampling rate and severe signal corruption, the category of a target of interest y can be recognized by seeking a sparse representation or linear combination of a small number of examples from a large library. A number of practically occurring phenomena, including variations in illumination angle, humidity, and co-adsorbate interactions can cause the linear mixture model to break down. Thus, similar to an approach for pose-invariant robust object recognition in computer vision (described by Wagner et al. in "Towards a Practical Face Recognition System: Robust Alignment and Illumination by Sparse Representation," IEEE Trans. on Pattern Analysis and Machine Intelligence (TPAMI), Vol. 34, No. 2, pp. 372-386, 2012 (hereinafter referred to as Wagner), which is hereby incorporated by reference as though fully set forth herein), the sparse demixing framework is extended to include nonlinear deformations due to different substrates and probe laser angle of incidence according to the following:

$$(x^*, e^*, \tau^*) = \underset{x,e}{\operatorname{argmin}} \|x\|_1 + \|e\|_1 \text{ subj. to } \|y \circ \tau - Ax - e\|_2^2 \leq \sigma^2.$$

Here, $y \in \mathbb{R}^d$ is the measured spectra at d wavelengths (with measurement noise variance $\sigma^2$), and $x \in \mathbb{R}^n$ is the set of sparse mixing coefficients with respect to the spectral library $A \in \mathbb{R}^{d \times n}$, whose columns represent spectral templates for n targets. The vector $e \in \mathbb{R}^d$ models sparse corrupted elements in the measured spectra y that cannot be well modeled by the library A, and τ models a class of deformations of the input signal y. Given a smooth parameterized function form for τ, this nonconvex optimization problem can be effectively solved for a large range of initial conditions by solving a sequence of convex optimizations problems that iteratively linearize about the current estimate of τ according to the following:

$$(x^*, e^*, \Delta\tau^*) = \underset{x,e,\Delta\tau}{\operatorname{argmin}} \|x\|_1 + \|e\|_1 \text{ subj. to } \|y \circ \tau^i + J\Delta\tau - Ax - e\|_2^2 \leq \sigma^2$$

$$\tau^{i+1} = \tau^i + \Delta\tau^*,$$

where $$J = \frac{\partial}{\partial \tau} y \circ \tau$$

is the Jacobian of y∘τ w.r.t. τ, and Δτ is the step in τ. As supported in Wagner, a large class of smooth deformations can be modeled and corrected using the above approach.

In FIG. 6, results are shown that demonstrate the large performance increase possible when the ICA algorithm is used to pre-filter the input to the SRC detection algorithm and the achievable optical PSNR is taken into account. These results show that ICA+SRC should be able to achieve Pd>92.7% with Pfa<0.01 % for PSNR of 20-25 dB. The ROC curves (recognition rate vs. false alarm rate) shown are the result of simulations done using either the SRC algorithm alone (represented by the dashed curve 600) or the combined ICA/SRC algorithm (represented by the solid curve 602), and assuming PSNRs that are easily achievable in hardware. In these simulations, random mixtures of 5 explosives that were randomly selected over many runs were detected from the 44 member URI explosives dataset. For each group of 5 spectra, 4 were designated as targets, and 1 was designated as clutter. Combining ICA with SRC (solid curve 602) dramatically improved the performance over SRC alone (dashed curve 600).

Additionally, it was noted that the result for SRC alone (dashed curve 600) was obtained for a spectrum with 538 samples uniformly spaced in wavenumbers in the range between 650 and 4000 cm$^{-1}$. In contrast, for the result obtained when both ICA and SRC were used (solid curve 602), the spectrum was obtained using variable spectral sample spacings (e.g., foveated sampling with only 88 wavenumber samples). Thus despite using 6.6× fewer measurements, ICA+SRC (solid curve 602) still greatly outperformed SRC alone (dashed curve 600).

In an embodiment of the present disclosure, ICA is used as a front end for SRC for spectral demixing, clutter rejection, modeling, and recognition of components in spectral mixtures measured using laser absorption spectroscopy. In another embodiment, nonuniform foveated sampling of both inputs to ICA+SRC and the library elements used by SRC to model the mixtures is used for reducing the number of measurements required and the computational complexity of the operations. In another embodiment, a separate SRC process is used on each of the selected outputs of ICA demixing, and the SRC processes are run in parallel on multiple processors. In another embodiment of the present disclosure, SRC is used to identify the spectral components in each selected ICA output by modeling, using the spectral library and compensating for spectral deformations. In another embodiment, the combination of ICA and SRC can be extended to other signals, non-limiting examples of which include radar waveforms, acoustic signals, and speech for clutter rejection, denoising, and recognition. Additionally, other blind source separation methods can be used instead of ICA as the front end to the SRC process. Non-limiting examples of such methods include sparse component analysis and non-negative matrix factorization.

In one embodiment, the present invention is applicable to remote sensing of materials and chemical residues. It can be used for hyperspectral imaging data analysis as well as spectral analysis. It is useful for analyzing satellite imagery and improved object recognition, such as in automotive active safety systems or automatic target recognition systems for self-guided weapons and airborne surveillance systems.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for analysis of spectral data, the system comprising:
   one or more processors and a non-transitory computer-readable medium having executable instructions encoded thereon such that when executed, the one or more processors perform operations of:
   separating a set of measured spectral mixtures using a blind demixing process, resulting in a plurality of demixed outputs;
   selecting a demixed output for further processing;
   selecting a spectral library in a set of spectral libraries that is specialized for the selected demixed output;
   classifying, via a non-blind demixing process, individual spectral components in the selected demixed output using the selected spectral library; and
   detecting trace chemical residues in the set of measured spectral mixtures.

2. The system as set forth in claim 1, wherein the blind demixing process is an Independent Component Analysis (ICA) process, and the non-blind demixing process is a Sparse Representation-based Classification (SRC) process.

3. The system as set forth in claim 2, wherein combined use of the ICA process and the SRC process separates spectra from the set of measured spectral mixtures and noise prior to classification of individual spectral components.

4. The system as set forth in claim 2, wherein the at least one demixed output, having a plurality of spectral features, is selected for further processing by the SRC process using similarity of spectral features in the at least one demixed output to a target spectra.

5. The system as set forth in claim 1, wherein spectral features in the selected demixed output are used to select the spectral library specialized for the selected demixed output.

6. The system as set forth in claim 2, wherein a separate SRC process is used on each selected demixed output, and the SRC processes are processed in parallel on multiple processors.

7. A computer-implemented method for analysis of spectral data, comprising:
   an act of causing one or more processors to execute instructions stored on a non-transitory memory such that upon execution, the one or more processors perform operations of:
   separating a set of measured spectral mixtures using a blind demixing process, resulting in a plurality of demixed outputs;
   selecting a demixed output for further processing;
   selecting a spectral library in a set of spectral libraries that is specialized for the selected demixed output;
   classifying, via a non-blind demixing process, individual spectral components in the selected demixed output using the selected spectral library; and
   detecting trace chemical residues in the set of measured spectral mixtures.

8. The method as set forth in claim 7, wherein the blind demixing process is an Independent Component Analysis (ICA) process, and the non-blind demixing process is a Sparse Representation-based Classification (SRC) process.

9. The method as set forth in claim 8, wherein combined use of the ICA process and the SRC process separates spectra from the set of measured spectral mixtures and noise prior to classification of individual spectral components.

10. The method as set forth in claim 8, wherein the at least one demixed output, having a plurality of spectral features, is selected for further processing by the SRC process using similarity of spectral features of the at least one demixed output to a target spectra.

11. The method as set forth in claim 7, wherein spectral features in the selected demixed output are used to select the spectral library specialized for the selected demixed output.

12. The method as set forth in claim 8, wherein a separate SRC process is used on each selected demixed output, and the SRC processes are processed in parallel on multiple processors.

13. A computer program product for analysis of spectral data, the computer program product comprising:
    computer-readable instructions stored on a non-transitory computer-readable medium that are executable by a computer having one or more processors for causing the processor to perform operations of:
        separating a set of measured spectral mixtures using a blind demixing process, resulting in a plurality of demixed outputs;
        selecting a demixed output for further processing;
        selecting a spectral library in a set of spectral libraries that is specialized for the selected demixed output;
        classifying, via a non-blind demixing process, individual spectral components in the selected demixed output using the selected spectral library and
        detecting trace chemical residues in the set of measured spectral mixtures.

14. The computer program as set forth in claim 13, wherein the blind demixing process is an Independent Component Analysis (ICA) process, and the non-blind demixing process is a Sparse Representation-based Classification (SRC) process.

15. The computer program product as set forth in claim 14, wherein combined use of the ICA process and the SRC process separates spectra from the set of measured spectral mixtures and noise prior to classification of individual spectral components.

16. The computer program as set forth in claim 14, wherein the at least one demixed output, having a plurality of spectral features, is selected for further processing by the SRC process using similarity of spectral features of the at least one demixed output to a target spectra.

17. The computer program as set forth in claim 13, wherein spectral features in the selected demixed output are used to select the spectral library specialized for the selected demixed output.

18. The computer program as set forth in claim 14, wherein a separate SRC process is used on each selected demixed output, and the SRC processes are processed in parallel on multiple processors.

* * * * *